(12) United States Patent
Fregnani et al.

(10) Patent No.: US 10,486,823 B2
(45) Date of Patent: Nov. 26, 2019

(54) FUEL BURN ADJUSTMENT BASED ON MEASURED LOWER HEATING VALUE

(71) Applicant: THE BOEING COMPANY, Chicago, IL (US)

(72) Inventors: Jose A. Fregnani, Distrito de Eugenio de Melo (BR); James D. Kinder, Renton, WA (US); Onofre Andrade, Distrito de Eugenio de Melo (BR)

(73) Assignee: The Boeing Company, Chicago, IL (US)

( * ) Notice: Subject to any disclaimer, the term of this patent is extended or adjusted under 35 U.S.C. 154(b) by 226 days.

(21) Appl. No.: 15/784,995

(22) Filed: Oct. 16, 2017

(65) Prior Publication Data

US 2019/0112067 A1    Apr. 18, 2019

(51) Int. Cl.
  *G06F 19/00*  (2018.01)
  *B64D 37/00*  (2006.01)
  (Continued)

(52) U.S. Cl.
  CPC .......... *B64D 37/005* (2013.01); *B64D 45/00* (2013.01); *G01C 21/00* (2013.01); *G01N 9/36* (2013.01);
  (Continued)

(58) Field of Classification Search
  CPC ...... B64D 37/005; B64D 45/00; G01C 21/00; G08G 5/0052; G08G 5/0021; G08G 5/0039; G01N 9/36
  (Continued)

(56) References Cited

U.S. PATENT DOCUMENTS 4,965,731 A * 10/1990 Weitz, Jr. .................. B64F 1/28
                                                    374/143
5,138,559 A *  8/1992 Kuehl .................. G01F 23/0076
                                                    340/618
(Continued)

FOREIGN PATENT DOCUMENTS

EP    2796956 A2   10/2014
EP    3065019 A1    9/2016
(Continued)

OTHER PUBLICATIONS

IATA 2007 Report on Alternative Fuels, pp. 1-68, Created Jan. 29, 2808.
(Continued)

*Primary Examiner* — Shardul D Patel
(74) *Attorney, Agent, or Firm* — Womble Bond Dickinson (US) LLP

(57) ABSTRACT

An aircraft is provided that includes a fuel storage tank for aviation fuel, and avionics systems interconnected by an avionics bus. The fuel storage tank receives aviation fuel during a fuel uplift for a flight according to a flight plan that includes and depends on a predicted fuel burn determined based on a reference lower heating value (LHV) of the aviation fuel. The avionics systems include temperature and density sensors, and a flight management system (FMS). The temperature and density sensors measure respectively the temperature and density of the aviation fuel. The FMS receives the measurements, estimates an actual LHV that is different from the reference LHV based on the measurements, and determines an adjusted predicted fuel burn for the flight based on the predicted fuel burn and the actual LHV. The FMS displays the adjusted predicted fuel burn and enable adjustment of the flight plan based thereon.

21 Claims, 4 Drawing Sheets

(51) Int. Cl.
*G01N 9/36* (2006.01)
*G08G 5/00* (2006.01)
*B64D 45/00* (2006.01)
*G01C 21/00* (2006.01)

(52) U.S. Cl.
CPC ......... *G08G 5/0021* (2013.01); *G08G 5/0039* (2013.01); *G08G 5/0052* (2013.01)

(58) Field of Classification Search
USPC ...... 701/100, 123; 208/16; 60/730, 772, 787
See application file for complete search history.

(56) References Cited

U.S. PATENT DOCUMENTS

| | | | | |
|---|---|---|---|---|
| 7,908,042 | B2* | 3/2011 | Brinkley | H04B 7/18506 342/29 |
| 2008/0183362 | A1* | 7/2008 | Dooley | F02C 3/20 701/100 |
| 2014/0005861 | A1* | 1/2014 | Mere | G08G 5/0039 701/3 |
| 2014/0104079 | A1* | 4/2014 | Bommer | G01F 23/0076 340/945 |
| 2015/0344148 | A1* | 12/2015 | Schwartz | B64D 37/005 701/123 |
| 2016/0260333 | A1* | 9/2016 | Gallo Olalla | G08G 5/0052 |

FOREIGN PATENT DOCUMENTS

| | | |
|---|---|---|
| EP | 3193268 A1 | 7/2017 |
| GB | 2176035 A | 12/1986 |

OTHER PUBLICATIONS

Argonne National Laboratory, "Life-Cycle Analysis Alternative Aviation Fuels in GREET", ANL/ESD/12-8, Energy Systems Division, pp. 1-76, Created Jun. 28, 2012.

International Search Report dated Jan. 28, 2019 in corresponding International Application No. PCT/IB2018/057936 filed Oct. 12, 2018.

* cited by examiner

FUEL BURN ADJUSTMENT BASED ON MEASURED LOWER HEATING VALUE

TECHNOLOGICAL FIELD

The present disclosure relates generally to aircraft fuel burn and, in particular, to the adjustment of fuel burn based on measured lower heating value of jet fuels produced from crude oil.

BACKGROUND

In the aerospace industry, aviation fuel is used to power aircraft. The aircraft burns fuel during flight, and in this context, fuel burn refers to the amount of fuel burned for the flight or a segment of the flight. A flight plan often includes and depends on a predicted fuel burn for the flight, and the predicted fuel burn is often determined based on an expected quality of the aviation fuel. In some cases, however, the fuel uplifted to the aircraft for a flight does not have the expected quality. This leads to fuel overburn, which may have a number of undesirable impacts on flight operations and operational costs. In one report, some long range flights frequently over burned 1500-2000 kilograms of aviation fuel, which represents a payload impact of about 20 passengers per flight. Some of these flights were diverted to enroute alternates due to reaching waypoints below minimum fuel requirements, which resulted in an additional operational cost.

The calorific content of aviation fuel is one measure of the quality of the fuel, and it may be expressed as a net calorific value—also known as a lower heating value (LHV). An investigation revealed that the Jet A-1 aviation fuel uplifted to the aircraft at departure stations presented a LHV of around 42.5 megajoules/kilogram (MJ/kg)—below specification for Jet A-1.

Therefore, it would be desirable to have a system and method that takes into account at least some of the issues discussed above, as well as other possible issues.

BRIEF SUMMARY

Example implementations of the present disclosure are directed to an aircraft and method in which a predicted fuel burn is adjusted based on a measured lower heating value (LHV). In accordance with example implementations, a flight management computer onboard the aircraft, and perhaps also a remote operations center, receive temperature and density measurements of aviation fuel uplifted to the aircraft, estimate an actual LHV based on the measurements, and adjust the predicted fuel burn accordingly. This enables adjustment of a flight plan for the aircraft using the adjusted predicted fuel burn, which may in turn avoid enroute diversions and the added operations costs resulting from enroute diversions.

The present disclosure thus includes, without limitation, the following example implementations.

Some example implementations provide an aircraft comprising a fuel storage tank for aviation fuel used to power the aircraft, the fuel storage tank being configured to receive aviation fuel during a fuel uplift for a flight according to a flight plan that includes and depends on a predicted fuel burn for the flight, the predicted fuel burn being determined based on a reference lower heating value (LHV) of the aviation fuel; and a plurality of avionics systems interconnected by an avionics bus, the plurality of avionics systems including: a temperature sensor configured to measure a temperature of the aviation fuel in the fuel storage tank after the fuel uplift, and output a temperature measurement corresponding thereto; a density sensor configured to measure a density of the aviation fuel in the fuel storage tank after the fuel uplift, and output a density measurement corresponding thereto; and a flight management system (FMS) configured to manage the flight plan during the flight, the FMS including: a flight management computer (FMC) configured to receive the temperature measurement and the density measurement, estimate an actual LHV that is different from the reference LHV based on the temperature measurement and the density measurement, and determine an adjusted predicted fuel burn for the flight based on the predicted fuel burn and the actual LHV; and a control display unit (CDU) configured to display the adjusted predicted fuel burn and enable adjustment of the flight plan based thereon.

In some example implementations of the aircraft of any preceding example implementation, or any combination of preceding example implementations, the plurality of avionics systems further includes a digital flight data acquisition unit (DFDAU) configured to receive and store the temperature measurement and the density measurement, and the FMC is configured to receive the temperature measurement and the density measurement from the DFDAU.

In some example implementations of the aircraft of any preceding example implementation, or any combination of preceding example implementations, the plurality of avionics systems further includes a datalink system configured to transmit the temperature measurement and the density measurement to an operations center configured to estimate the actual LHV and determine the adjusted predicted fuel burn, and produce an adjusted flight plan for the flight based on the adjusted predicted fuel burn, and wherein the datalink system is configured to receive the adjusted flight plan from the operations center, and the FMS is configured to replace the flight plan with the adjusted flight plan, and manage the adjusted flight plan during the flight.

In some example implementations of the aircraft of any preceding example implementation, or any combination of preceding example implementations, the FMC being configured to estimate the actual LHV includes being configured to determine a specific gravity of the aviation fuel in the fuel storage tank based on the temperature measurement and the density measurement, and estimate the actual LHV based on the specific gravity and a known linear relationship between specific gravity and LHV.

In some example implementations of the aircraft of any preceding example implementation, or any combination of preceding example implementations, the FMC being configured to determine the specific gravity of the aviation fuel includes being configured to determine the specific gravity SG according to the following:

$$SG=(0.0063(T\text{fuel}-15.56)+\rho)/8.3282$$

where Tfuel represents the temperature measurement, and $\rho$ represents the density measurement.

In some example implementations of the aircraft of any preceding example implementation, or any combination of preceding example implementations, the known linear relationship is expressed as a linear function having a slope M and an intercept B, and the FMC being configured to estimate the actual LHV includes being configured to estimate the actual LHV according to the following:

$$LHV=M\times SG+B$$

where SG represents the specific gravity.

In some example implementations of the aircraft of any preceding example implementation, or any combination of preceding example implementations, the predicted fuel burn is determined based on a standard fuel flow, and the FMC being configured to determine the adjusted predicted fuel burn includes being configured to determine a corrected fuel flow and determine the adjusted predicted fuel burn based thereon, the corrected fuel flow Wfcor being determined according to the following:

$$Wfcor=Wf(LHVref/LHV)$$

where Wf represents the standard fuel flow, and LHVref represents the reference LHV.

Some example implementations provide a method of determining an adjusted predicted fuel burn for a flight of an aircraft according to a flight plan that includes and depends on a predicted fuel burn for the flight, and enabling adjustment of the flight plan based thereon, the aircraft including a fuel storage tank for aviation fuel used to power the aircraft, the fuel storage tank being configured to receive aviation fuel during a fuel uplift for the flight, the predicted fuel burn being determined based on a reference lower heating value (LHV) of the aviation fuel, the method comprising measuring a temperature of the aviation fuel in the fuel storage tank after the fuel uplift, and outputting a temperature measurement corresponding thereto, using a temperature sensor of a plurality of avionics systems of the aircraft interconnected by an avionics bus, the plurality of avionics systems also including a density sensor, and a flight management system (FMS) configured to manage the flight plan during the flight, the FMS including a flight management computer (FMC) and a control display unit (CDU); measuring a density of the aviation fuel in the fuel storage tank after the fuel uplift, and outputting a density measurement corresponding thereto, using the density sensor; estimating an actual LHV that is different from the reference LHV based on the temperature measurement and the density measurement, and determining an adjusted predicted fuel burn for the flight based on the predicted fuel burn and the actual LHV, using the FMC; and displaying the adjusted predicted fuel burn and enabling adjustment of the flight plan based thereon, using the CDU.

Some example implementations provide a method of operating an aircraft for a flight of the aircraft according to a flight plan that includes and depends on a predicted fuel burn for the flight, the aircraft including a fuel storage tank for aviation fuel used to power the aircraft, the fuel storage tank being configured to receive aviation fuel during a fuel uplift for the flight, the predicted fuel burn being determined based on a reference lower heating value (LHV) of the aviation fuel, the method comprising measuring a temperature of the aviation fuel in the fuel storage tank after the fuel uplift, and outputting a temperature measurement corresponding thereto, using a temperature sensor of a plurality of avionics systems of the aircraft interconnected by an avionics bus, the plurality of avionics systems also including a density sensor, and a flight management system (FMS) configured to manage the flight plan during the flight, the FMS including a flight management computer (FMC); measuring a density of the aviation fuel in the fuel storage tank after the fuel uplift, and outputting a density measurement corresponding thereto, using the density sensor; estimating an actual LHV that is different from the reference LHV based on the temperature measurement and the density measurement, and determining an adjusted predicted fuel burn for the flight based on the predicted fuel burn and the actual LHV, using the FMC; producing an adjusted flight plan for the flight based on the adjusted predicted fuel burn; and managing the adjusted flight plan during the flight using the FMS.

In some example implementations of the method of any preceding example implementation, or any combination of preceding example implementations, the plurality of avionics systems further includes a digital flight data acquisition unit (DFDAU), and the method further comprises receiving and storing the temperature measurement and the density measurement using the DFDAU, the FMC receiving the temperature measurement and the density measurement from the DFDAU.

In some example implementations of the method of any preceding example implementation, or any combination of preceding example implementations, the plurality of avionics systems further includes a datalink system, and the method further comprises transmitting the temperature measurement and the density measurement to an operations center using the datalink system, the operations center estimating the actual LHV and determine the adjusted predicted fuel burn, and producing an adjusted flight plan for the flight based on the adjusted predicted fuel burn; receiving the adjusted flight plan from the operations center using the datalink system; and replacing the flight plan with the adjusted flight plan, and managing the adjusted flight plan during the flight, using the FMS.

In some example implementations of the method of any preceding example implementation, or any combination of preceding example implementations, estimating the actual LHV includes determining a specific gravity of the aviation fuel in the fuel storage tank based on the temperature measurement and the density measurement, and estimating the actual LHV based on the specific gravity and a known linear relationship between specific gravity and LHV.

In some example implementations of the method of any preceding example implementation, or any combination of preceding example implementations, determining the specific gravity of the aviation fuel includes determining the specific gravity SG according to the following:

$$SG=(0.0063(Tfuel-15.56)+\rho)/8.3282$$

where Tfuel represents the temperature measurement, and ρ represents the density measurement.

In some example implementations of the method of any preceding example implementation, or any combination of preceding example implementations, the known linear relationship is expressed as a linear function having a slope M and an intercept B, and estimating the actual LHV includes estimating the actual LHV according to the following:

$$LHV=M \times SG+B$$

where SG represents the specific gravity.

In some example implementations of the method of any preceding example implementation, or any combination of preceding example implementations, the predicted fuel burn is determined based on a standard fuel flow, and determining the adjusted predicted fuel burn includes determining a corrected fuel flow and determining the adjusted predicted fuel burn based thereon, the corrected fuel flow Wfcor being determined according to the following:

$$Wfcor=Wf(LHVref/LHV)$$

where Wf represents the standard fuel flow, and LHVref represents the reference LHV.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described example implementations of the disclosure in general terms, reference will now be made to the accompanying drawings, which are not necessarily drawn to scale, and wherein:

DETAILED DESCRIPTION

Figure 1:
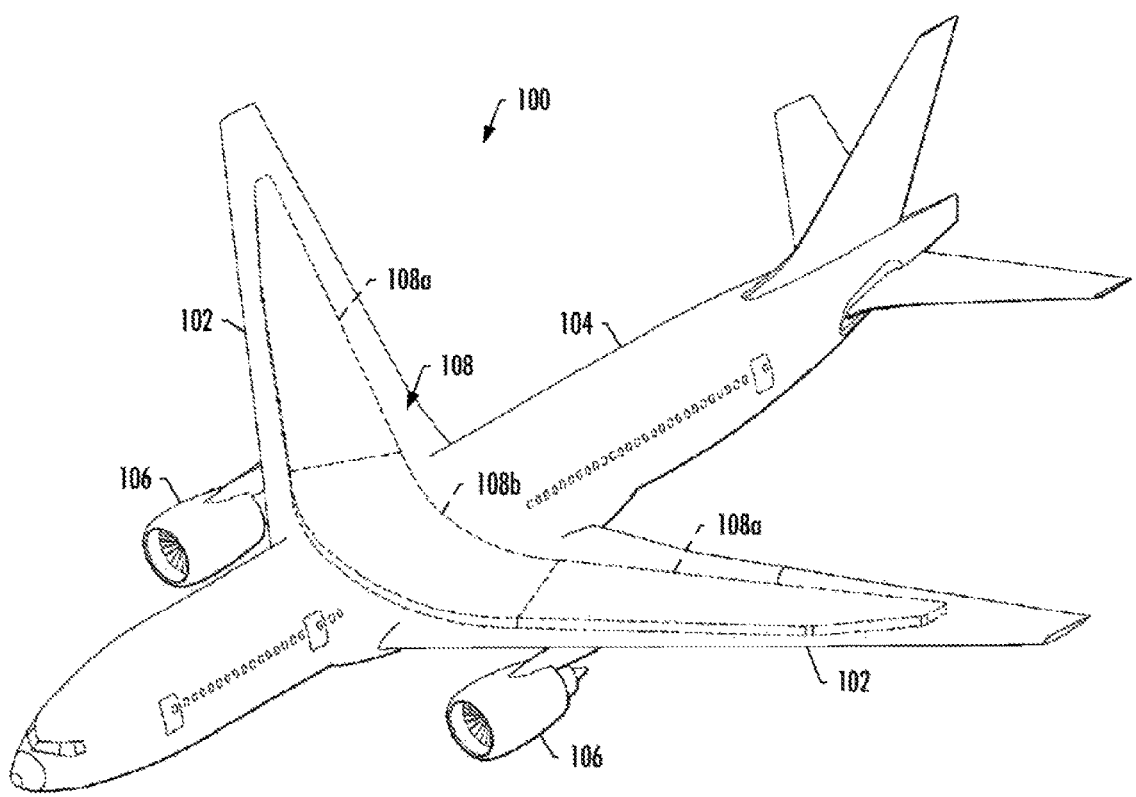
FIG. 1 illustrates an aircraft according to example implementations of the present disclosure.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. For example, unless otherwise indicated, reference something as being a first, second or the like should not be construed to imply a particular order. Also, something may be described as being above something else (unless otherwise indicated) may instead be below, and vice versa; and similarly, something described as being to the left of something else may instead be to the right, and vice versa. Like reference numerals refer to like elements throughout.

As explained in the Background section, the calorific content of aviation fuel is one measure of the quality of the fuel, and it may be expressed as a net calorific value—also known as a lower heating value (LHV). Example implementations of the present disclosure are generally directed to aircraft fuel burn and, in particular, to the adjustment of fuel burn based on a measured LHV, which may be expressed in British thermal units per pound (BTU/lb).

Example implementations may be applicable to any of a number of different types, makes and models of aircraft. FIG. 1 illustrates one example of a suitable type of aircraft 100. As shown, the aircraft has wings 102 attached to body 104 and includes engines 106 attached to respective ones of the wings. The aircraft also includes one or more fuel storage tanks 108 for aviation fuel used to power the aircraft. As shown, in some examples, the fuel storage tanks include main fuel storage tanks 108*a* in the wings, and a center fuel storage tank 108*b* in the body.

Figure 2:
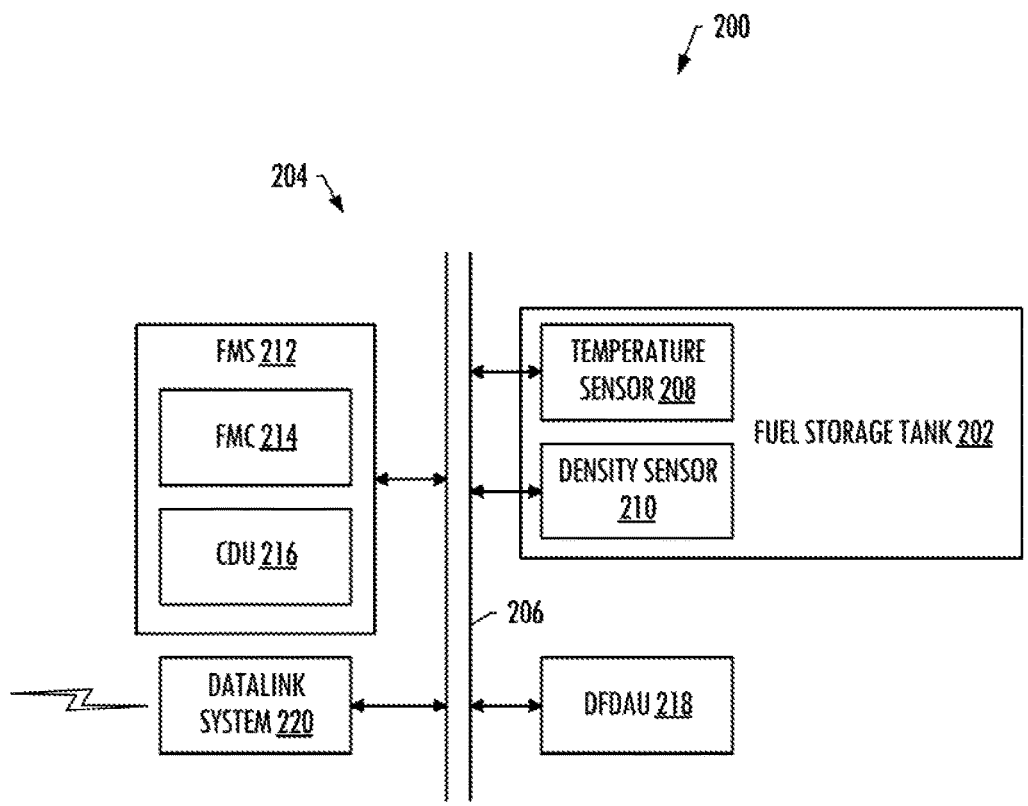
FIG. 2 illustrates an aircraft that in some example implementations corresponds to the aircraft of FIG. 1.

FIG. 2 illustrates an aircraft 200 that in some example implementations corresponds to the aircraft 100 of FIG. 1. It should be understood that the figure illustrates only those components of the aircraft that may be pertinent to example implementations of the present disclosure. The aircraft may include additional or alternative components, such as those more particularly illustrated in FIG. 1 (e.g., wings 102, body 104 and engines 106).

As shown in FIG. 2, the aircraft 200 includes a fuel storage tank 202 that in some examples corresponds to fuel storage tank 108. In various examples, the fuel storage tank 202 may be a main fuel storage tank 108*a* or a center fuel storage tank 108*b*. According to example implementations, the fuel storage tank is configured to receive aviation fuel during a fuel uplift for a flight according to a flight plan that includes and depends on a predicted fuel burn for the flight. The predicted fuel burn is determined based on a reference LHV of the aviation fuel (baseline for standard performance computations), which may be expressed in BTU/lb.

As also shown, the aircraft 200 includes a plurality of avionics systems 204 interconnected by an avionics bus 206. The plurality of avionics systems include a temperature sensor 208, a density sensor 210 and a flight management system (FMS) 212. The temperature sensor is configured to measure a temperature of the aviation fuel in the fuel storage tank 202 after the fuel uplift, and output a temperature measurement corresponding thereto. Similarly, the density sensor configured to measure a density of the aviation fuel in the fuel storage tank after the fuel uplift, and output a density measurement corresponding thereto. In various examples, the temperature may be expressed in degrees Celsius (° C.), and the density may be expressed in pounds per gallon (lb/Gal).

The FMS 212 is configured to manage the flight plan during the flight of the aircraft 200. The FMS includes a flight management computer (FMC) 214 and a control display unit (CDU) 216. In accordance with example implementations of the present disclosure, the FMC is configured to receive the temperature measurement and the density measurement of the aviation fuel in the fuel storage tank 202. The FMC is configured to estimate or otherwise calculate an actual LHV that is different from the reference LHV based on the temperature measurement and the density measurement, and determine an adjusted predicted fuel burn for the flight based on the predicted fuel burn and the actual LHV. The CDU is configured to display the adjusted predicted fuel burn and enable adjustment of the flight plan based thereon.

In some examples, the plurality of avionics systems 204 further includes a digital flight data acquisition unit (DFDAU) 218 configured to receive and store the temperature measurement and the density measurement. In some of these examples, the FMC 214 is configured to receive the temperature measurement and the density measurement from the DFDAU.

In some examples, the plurality of avionics systems 204 further includes a datalink system 220 configured to transmit the temperature measurement and the density measurement to an operations center. The operations center is configured to estimate the actual LHV and determine the adjusted predicted fuel burn, and produce an adjusted flight plan for the flight based on the adjusted predicted fuel burn. The datalink system, then, is configured to receive the adjusted flight plan from the operations center. And the FMS 212 is configured to replace the flight plan with the adjusted flight plan, and manage the adjusted flight plan during the flight.

The FMC 214 may estimate the actual LHV in any of a number of different manners. In some examples, the FMC is configured to determine a specific gravity of the aviation fuel in the fuel storage tank 202 based on the temperature measurement and the density measurement, and estimate the actual LHV based on the specific gravity and a known linear relationship between specific gravity and LHV. In some further examples, the FMC is configured to determine the specific gravity SG according to the following:

$$SG=(0.0063(Tfuel-15.56)+\rho)/8.3282$$

where Tfuel represents the temperature measurement, and $\rho$ represents the density measurement. Additionally or alternatively, in some further examples, the known linear relationship is expressed as a linear function having a slope M and an intercept B, and the FMC is configured to estimate the actual LHV according to the following:

$$LHV=M \times SG+B$$

where SG represents the specific gravity. In some examples, M and B may be set at default values such as respectively −5,220 and 22,777.

In some examples, the predicted fuel burn is determined based on a standard fuel flow. The standard fuel flow refers to a calculated flow rate of the aviation fuel, and it may be expressed in pounds or kilograms per hour (lb/h or kg/h). The standard fuel flow may be calculated for a current gross weight, altitude, Mach number and International Standard Atmosphere (ISA) deviation, such as via FMC performance tables. In these examples, the FMC 214 is configured to determine a corrected fuel flow (e.g., lb/h or kg/h) and determine the adjusted predicted fuel burn based thereon. The corrected fuel flow is an adjusted flow rate relative to the standard fuel flow based on the actual LHV relative to the reference LHV; and in some examples, the corrected fuel flow Wfcor is determined according to the following:

$$Wfcor=Wf\ (LHVref/LHV)$$

where Wf represents the standard fuel flow, and LHVref represents the reference LHV. In some examples, LHVref may be set at a default value such as 18,590 BTU/lb. The relation LHVref/LHV is the so-called fuel flow factor FFfac.

The predicted fuel burn and adjusted predicted fuel burn may be for the entire flight or for each of one or more segments of the flight, with each segment being defined between successive waypoints. In some examples, then, the FMC 214 may adjust the predicted fuel burn AFref between successive waypoints i and j along the flight route through a direct relation with FFfac as follows:

$$\Delta F(i, j)=FFfac \times \Delta Fref(i, j)$$

where $\Delta F(i, j)$ represents the adjusted predicted fuel burn between waypoints i and j, considering the default LHVref.

In a flight planning system at the operations center, the adjusted predicted fuel burn $\Delta F$ for a given sector j defined between two subsequent waypoints along the route may be calculated via integration of the corrected fuel flow Wfcor at each computation cycle $\Delta t$ according to the following:

$$\Delta F(j) = \int_0^T Wfcor(t) \times dt \sim \sum_{i=1}^{N=T/\Delta t} Wfcor(i) \times \Delta t = \sum_{i=1}^{N} Wf(i) \times \left(\frac{LHVref}{LHV}\right) \times \Delta t$$

In the preceding, T represents an estimated time to fly between waypoints (e.g., in seconds) based on a predicted Mach number measured at j waypoint, and $\Delta t$ is the integration time (e.g., in seconds) that may be defined in the flight planning system. Also in the preceding, the standard fuel flow at waypoint i, Wf(i), may be determined as a function of a current gross weight GW, altitude ALT, Mach number M and ISA deviation ISAdev at integration point i:

$$Wf(i)=f\ (GW(i), M(i), ISAdev(i), ALT(i))$$

The gross weight GW(i) may be determined as follows:

$$GW(i)=GW(i-1)-Wf(i-1).\ (LHVref/LHV)$$

For a flight plan including N sectors, the adjusted predicted fuel burn $\Delta F$ over the flight may be determined by summation of $\Delta F(j)$ at N sectors as follows:

$$F = \sum_{j=1}^{N} \Delta F(j)$$

Figure 3:
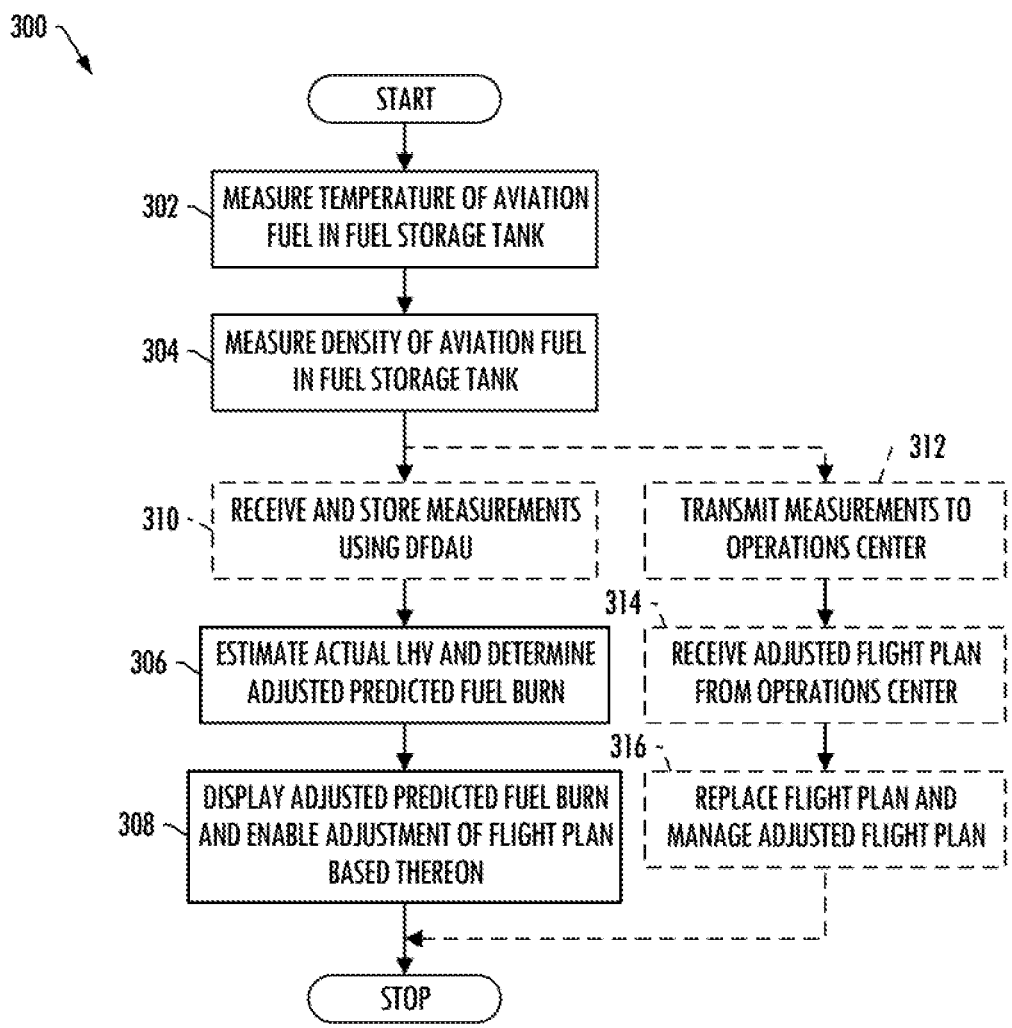
FIG. 3 is a flowchart illustrating various steps in a method of determining an adjusted predicted fuel burn for a flight of an aircraft, according to various example implementations.

FIG. 3 is a flowchart illustrating various steps in a method 300 of determining an adjusted predicted fuel burn for a flight of an aircraft 200 according to a flight plan that includes and depends on a predicted fuel burn for the flight, and enabling adjustment of the flight plan based thereon, according to example implementations of the present disclosure. As described above, the aircraft includes a fuel storage tank 202 for aviation fuel used to power the aircraft. The fuel storage tank is configured to receive aviation fuel during a fuel uplift for the flight. And the predicted fuel burn is determined based on a reference LHV of the aviation fuel As shown at block 302, the method 300 includes measuring a temperature of the aviation fuel in the fuel storage tank 202 after the fuel uplift, and outputting a temperature measurement corresponding thereto. This is accomplished using a temperature sensor 208 of a plurality of avionics systems 204 of the aircraft 200 interconnected by an avionics bus 206. Again, the plurality of avionics systems also include a density sensor 210, and a FMS 212 configured to manage the flight plan during the flight, with the FMS including a FMC 214 and a CDU 216.

As shown at block 304, the method 300 includes measuring a density of the aviation fuel in the fuel storage tank 202 after the fuel uplift, and outputting a density measurement corresponding thereto. This is accomplished using the density sensor 210.

The method 300 includes estimating an actual LHV that is different from the reference LHV based on the temperature measurement and the density measurement, and determining an adjusted predicted fuel burn for the flight based on the predicted fuel burn and the actual LHV, using the FMC

214, as shown at block 306. And the method includes displaying the adjusted predicted fuel burn and enabling adjustment of the flight plan based thereon, using the CDU 216, as shown at block 308.

In some examples in which the plurality of avionics systems 204 further includes a digital flight data acquisition unit (DFDAU) 218, the method further includes receiving and storing the temperature measurement and the density measurement using the DFDAU, as shown at block 310. In some of these examples, the FMC 214 receives the temperature measurement and the density measurement from the DFDAU.

In some examples in which the plurality of avionics systems 204 further includes a datalink system 220, the method further includes transmitting the temperature measurement and the density measurement to an operations center using the datalink system, as shown at block 312. The operations center estimates the actual LHV and determines the adjusted predicted fuel burn, and produces an adjusted flight plan for the flight based on the adjusted predicted fuel burn. The method then also includes receiving the adjusted flight plan from the operations center using the datalink system, as shown at block 314; and replacing the flight plan with the adjusted flight plan, and managing the adjusted flight plan during the flight, using the FMS 212, as shown at block 316.

Figure 4:
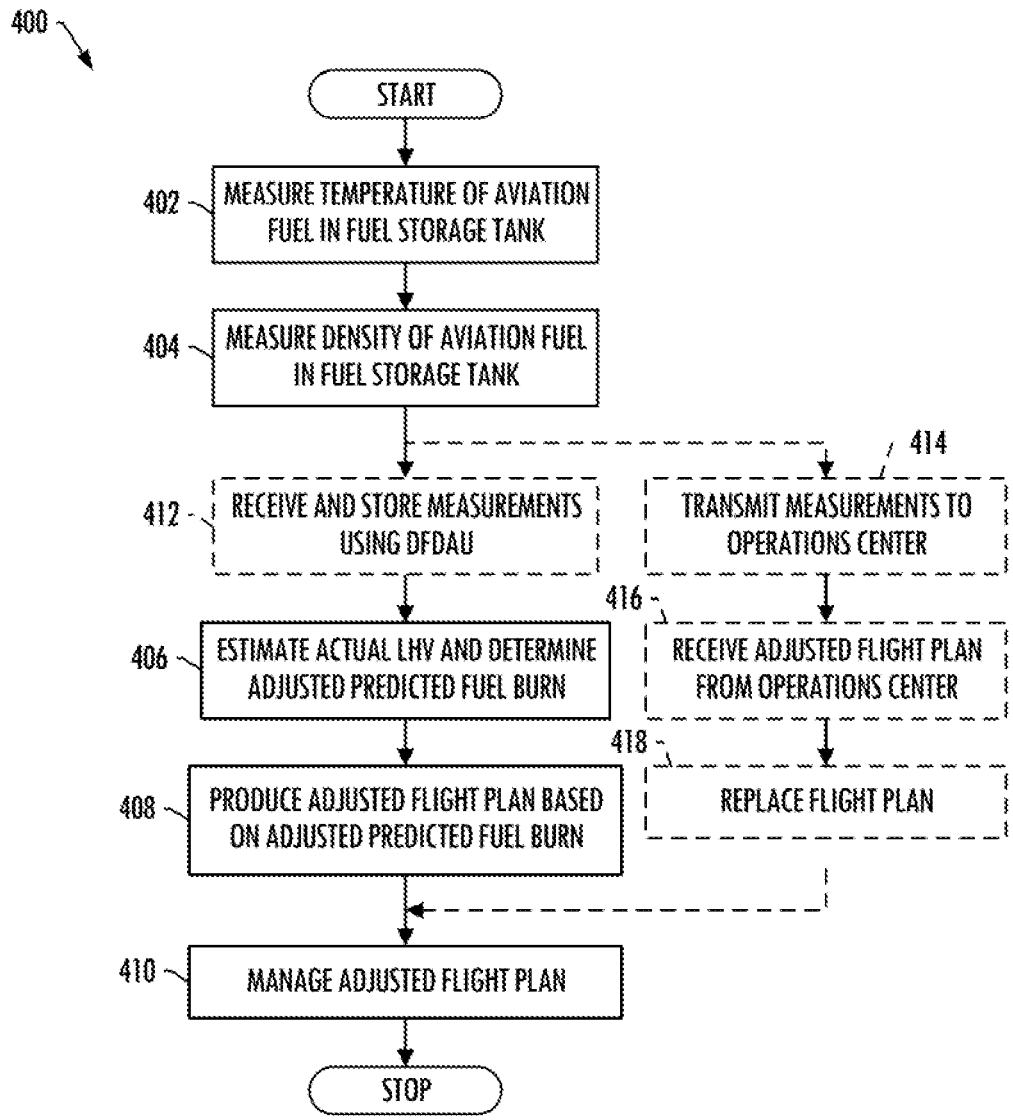
FIG. 4 is a flowchart illustrating various steps in a method of operating an aircraft for a flight of the aircraft, according to various example implementations.

FIG. 4 is a flowchart illustrating various steps in a method 400 of operating an aircraft 200 for a flight of the aircraft according to a flight plan that includes and depends on a predicted fuel burn for the flight, and enabling adjustment of the flight plan based thereon, according to example implementations of the present disclosure. As described above, the aircraft includes a fuel storage tank 202 for aviation fuel used to power the aircraft. The fuel storage tank is configured to receive aviation fuel during a fuel uplift for the flight. And the predicted fuel burn is determined based on a reference LHV of the aviation fuel As shown at block 402, the method 400 includes measuring a temperature of the aviation fuel in the fuel storage tank 202 after the fuel uplift, and outputting a temperature measurement corresponding thereto. This is accomplished using a temperature sensor 208 of a plurality of avionics systems 204 of the aircraft 200 interconnected by an avionics bus 206. Again, the plurality of avionics systems also include a density sensor 210, and a FMS 212 configured to manage the flight plan during the flight, with the FMS including a FMC 214.

As shown at block 404, the method 400 includes measuring a density of the aviation fuel in the fuel storage tank 202 after the fuel uplift, and outputting a density measurement corresponding thereto. This is accomplished using the density sensor 210.

The method 400 includes estimating an actual LHV that is different from the reference LHV based on the temperature measurement and the density measurement, and determining an adjusted predicted fuel burn for the flight based on the predicted fuel burn and the actual LHV, using the FMC 214, as shown at block 406. The method includes producing an adjusted flight plan for the flight based on the adjusted predicted fuel burn, and managing the adjusted flight plan during the flight using the FMS 212, as shown at blocks 408 and 410.

In some examples in which the plurality of avionics systems 204 further includes a digital flight data acquisition unit (DFDAU) 218, the method further includes receiving and storing the temperature measurement and the density measurement using the DFDAU, as shown at block 412. In some of these examples, the FMC 214 receives the temperature measurement and the density measurement from the DFDAU.

In some examples in which the plurality of avionics systems 204 further includes a datalink system 220, the method further includes transmitting the temperature measurement and the density measurement to an operations center using the datalink system, as shown at block 414. The operations center estimates the actual LHV and determines the adjusted predicted fuel burn, and produces the adjusted flight plan for the flight based on the adjusted predicted fuel burn. The method then also includes receiving the adjusted flight plan from the operations center using the datalink system, as shown at block 416; and replacing the flight plan with the adjusted flight plan, as shown at block 418.

According to example implementations of the present disclosure, the FMC 214 may be implemented by various means. Means for implementing the FMC may include hardware, alone or under direction of one or more computer programs from a computer-readable storage medium. In some examples, the FMC includes one or more of each of a number of components such as, for example, a processor (e.g., processing circuitry) connected to a memory (e.g., storage device). The processor is generally any piece of computer hardware that is capable of processing information such as, for example, data, computer programs and/or other suitable electronic information.

The memory is generally any piece of computer hardware that is capable of storing information such as, for example, data, computer programs (e.g., computer-readable program code) and/or other suitable information either on a temporary basis and/or a permanent basis. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

As explained above, computer-readable program code or instructions may be stored in memory, and executed by a processor that is thereby programmed, to implement functions of the FMC 214 described herein. As will be appreciated, any suitable program code instructions may be loaded onto the FMC from a computer-readable storage medium to produce a particular machine, such that the particular machine becomes a means for implementing the functions specified herein. These program code instructions may also be stored in a computer-readable storage medium that can direct the FMC, a processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into the FMC, a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the FMC 214, computer, processor or other programmable apparatus provide operations for implementing functions described herein.

Execution of instructions by a processor, or storage of instructions in a computer-readable storage medium, supports combinations of operations for performing the specified functions. In this manner, the FMC 214 may include a processor and a computer-readable storage medium or memory coupled to the processor, where the processor is configured to execute computer-readable program code stored in the memory. It will also be understood that one or more functions, and combinations of functions, may be implemented by other special purpose hardware-based computer systems and/or processors which perform the specified functions, or combinations of special purpose hardware and program code instructions.

Many modifications and other implementations of the disclosure set forth herein will come to mind to one skilled in the art to which the disclosure pertains having the benefit of the teachings presented in the foregoing description and the associated drawings. Therefore, it is to be understood that the disclosure is not to be limited to the specific implementations disclosed and that modifications and other implementations are intended to be included within the scope of the appended claims. Moreover, although the foregoing description and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aircraft comprising:
   a fuel storage tank for aviation fuel used to power the aircraft, the fuel storage tank being configured to receive aviation fuel during a fuel uplift for a flight according to a flight plan that includes and depends on a predicted fuel burn for the flight, the predicted fuel burn being determined based on a reference lower heating value (LHV) of the aviation fuel; and
   a plurality of avionics systems interconnected by an avionics bus, the plurality of avionics systems including:
      a temperature sensor configured to measure a temperature of the aviation fuel in the fuel storage tank after the fuel uplift, and output a temperature measurement corresponding thereto;
      a density sensor configured to measure a density of the aviation fuel in the fuel storage tank after the fuel uplift, and output a density measurement corresponding thereto; and
      a flight management system (FMS) configured to manage the flight plan during the flight, the FMS including:
         a flight management computer (FMC) configured to receive the temperature measurement and the density measurement, estimate an actual LHV that is different from the reference LHV based on the temperature measurement and the density measurement, and determine an adjusted predicted fuel burn for the flight based on the predicted fuel burn and the actual LHV; and
      a control display unit (CDU) configured to display the adjusted predicted fuel burn and enable adjustment of the flight plan based thereon.

2. The aircraft of claim 1, wherein the plurality of avionics systems further includes a digital flight data acquisition unit (DFDAU) configured to receive and store the temperature measurement and the density measurement, and the FMC is configured to receive the temperature measurement and the density measurement from the DFDAU.

3. The aircraft of claim 1, wherein the plurality of avionics systems further includes a datalink system configured to transmit the temperature measurement and the density measurement to an operations center configured to estimate the actual LHV and determine the adjusted predicted fuel burn, and produce an adjusted flight plan for the flight based on the adjusted predicted fuel burn, and
   wherein the datalink system is configured to receive the adjusted flight plan from the operations center, and the FMS is configured to replace the flight plan with the adjusted flight plan, and manage the adjusted flight plan during the flight.

4. The aircraft of claim 1, wherein the FMC being configured to estimate the actual LHV includes being configured to determine a specific gravity of the aviation fuel in the fuel storage tank based on the temperature measurement and the density measurement, and estimate the actual LHV based on the specific gravity and a known linear relationship between specific gravity and LHV.

5. The aircraft of claim 4, wherein the FMC being configured to determine the specific gravity of the aviation fuel includes being configured to determine the specific gravity SG according to the following:

$$SG=(0.0063(T\text{fuel}-15.56)+\rho)/8.3282$$

where Tfuel represents the temperature measurement, and $\rho$ represents the density measurement.

6. The aircraft of claim 4, wherein the known linear relationship is expressed as a linear function having a slope M and an intercept B, and the FMC being configured to estimate the actual LHV includes being configured to estimate the actual LHV according to the following:

$$LHV=M \times SG+B$$

where SG represents the specific gravity.

7. The aircraft of claim 1, wherein the predicted fuel burn is determined based on a standard fuel flow, and the FMC being configured to determine the adjusted predicted fuel burn includes being configured to determine a corrected fuel flow and determine the adjusted predicted fuel burn based thereon, the corrected fuel flow Wfcor being determined according to the following:

$$W\!f\text{cor}=W\!f\,(LHVref/LHV)$$

where Wf represents the standard fuel flow, and LHVref represents the reference LHV.

8. A method of determining an adjusted predicted fuel burn for a flight of an aircraft according to a flight plan that includes and depends on a predicted fuel burn for the flight, and enabling adjustment of the flight plan based thereon, the aircraft including a fuel storage tank for aviation fuel used to power the aircraft, the fuel storage tank being configured to receive aviation fuel during a fuel uplift for the flight, the predicted fuel burn being determined based on a reference lower heating value (LHV) of the aviation fuel, the method comprising:

measuring a temperature of the aviation fuel in the fuel storage tank after the fuel uplift, and outputting a temperature measurement corresponding thereto, using a temperature sensor of a plurality of avionics systems of the aircraft interconnected by an avionics bus, the plurality of avionics systems also including a density sensor, and a flight management system (FMS) configured to manage the flight plan during the flight, the FMS including a flight management computer (FMC) and a control display unit (CDU);

measuring a density of the aviation fuel in the fuel storage tank after the fuel uplift, and outputting a density measurement corresponding thereto, using the density sensor;

estimating an actual LHV that is different from the reference LHV based on the temperature measurement and the density measurement, and determining an adjusted predicted fuel burn for the flight based on the predicted fuel burn and the actual LHV, using the FMC; and displaying the adjusted predicted fuel burn and enabling adjustment of the flight plan based thereon, using the CDU.

9. The method of claim 8, wherein the plurality of avionics systems further includes a digital flight data acquisition unit (DFDAU), and the method further comprises:

receiving and storing the temperature measurement and the density measurement using the DFDAU, the FMC receiving the temperature measurement and the density measurement from the DFDAU.

10. The method of claim 8, wherein the plurality of avionics systems further includes a datalink system, and the method further comprises:

transmitting the temperature measurement and the density measurement to an operations center using the datalink system, the operations center estimating the actual LHV and determine the adjusted predicted fuel burn, and producing an adjusted flight plan for the flight based on the adjusted predicted fuel burn;

receiving the adjusted flight plan from the operations center using the datalink system; and replacing the flight plan with the adjusted flight plan, and managing the adjusted flight plan during the flight, using the FMS.

11. The method of claim 8, wherein estimating the actual LHV includes determining a specific gravity of the aviation fuel in the fuel storage tank based on the temperature measurement and the density measurement, and estimating the actual LHV based on the specific gravity and a known linear relationship between specific gravity and LHV.

12. The method of claim 11, wherein determining the specific gravity of the aviation fuel includes determining the specific gravity SG according to the following:

$$SG=(0.0063(Tfuel-15.56)+\rho)/8.3282$$

where Tfuel represents the temperature measurement, and $\rho$ represents the density measurement.

13. The method of claim 11, wherein the known linear relationship is expressed as a linear function having a slope M and an intercept B, and estimating the actual LHV includes estimating the actual LHV according to the following:

$$LHV=M \times SG+B$$

where SG represents the specific gravity.

14. The method of claim 8, wherein the predicted fuel burn is determined based on a standard fuel flow, and determining the adjusted predicted fuel burn includes determining a corrected fuel flow and determining the adjusted predicted fuel burn based thereon, the corrected fuel flow Wfcor being determined according to the following:

$$Wfcor=Wf\,(LHVref/LHV)$$

where Wf represents the standard fuel flow, and LHVref represents the reference LHV.

15. A method of operating an aircraft for a flight of the aircraft according to a flight plan that includes and depends on a predicted fuel burn for the flight, the aircraft including a fuel storage tank for aviation fuel used to power the aircraft, the fuel storage tank being configured to receive aviation fuel during a fuel uplift for the flight, the predicted fuel burn being determined based on a reference lower heating value (LHV) of the aviation fuel, the method comprising:

measuring a temperature of the aviation fuel in the fuel storage tank after the fuel uplift, and outputting a temperature measurement corresponding thereto, using a temperature sensor of a plurality of avionics systems of the aircraft interconnected by an avionics bus, the plurality of avionics systems also including a density sensor, and a flight management system (FMS) configured to manage the flight plan during the flight, the FMS including a flight management computer (FMC);

measuring a density of the aviation fuel in the fuel storage tank after the fuel uplift, and outputting a density measurement corresponding thereto, using the density sensor;

estimating an actual LHV that is different from the reference LHV based on the temperature measurement and the density measurement, and determining an adjusted predicted fuel burn for the flight based on the predicted fuel burn and the actual LHV, using the FMC;

producing an adjusted flight plan for the flight based on the adjusted predicted fuel burn; and managing the adjusted flight plan during the flight using the FMS.

16. The method of claim 15, wherein the plurality of avionics systems further includes a digital flight data acquisition unit (DFDAU), and the method further comprises:

receiving and storing the temperature measurement and the density measurement using the DFDAU, the FMC receiving the temperature measurement and the density measurement from the DFDAU.

17. The method of claim 15, wherein the plurality of avionics systems further includes a datalink system, and the method further comprises:

transmitting the temperature measurement and the density measurement to an operations center using the datalink system, the operations center estimating the actual LHV and determine the adjusted predicted fuel burn, and producing the adjusted flight plan for the flight based on the adjusted predicted fuel burn;

receiving the adjusted flight plan from the operations center using the datalink system; and replacing the flight plan with the adjusted flight plan.

18. The method of claim 15, wherein estimating the actual LHV includes determining a specific gravity of the aviation fuel in the fuel storage tank based on the temperature measurement and the density measurement, and estimating the actual LHV based on the specific gravity and a known linear relationship between specific gravity and LHV.

19. The method of claim 18, wherein determining the specific gravity of the aviation fuel includes determining the specific gravity SG according to the following:

$$SG=(0.0063(T\text{fuel}-15.56)+\rho)/8.3282$$

where Tfuel represents the temperature measurement, and $\rho$ represents the density measurement.

20. The method of claim 18, wherein the known linear relationship is expressed as a linear function having a slope M and an intercept B, and estimating the actual LHV includes estimating the actual LHV according to the following:

$$LHV = M \times SG + B$$

where SG represents the specific gravity.

21. The method of claim 15, wherein the predicted fuel burn is determined based on a standard fuel flow, and determining the adjusted predicted fuel burn includes determining a corrected fuel flow and determining the adjusted predicted fuel burn based thereon, the corrected fuel flow Wfcor being determined according to the following:

$$Wf\text{cor} = Wf\,(LHVref/LHV)$$

where Wf represents the standard fuel flow, and LHVref represents the reference LHV.

* * * * *